United States Patent
Barreca et al.

(10) Patent No.: US 8,193,386 B2
(45) Date of Patent: Jun. 5, 2012

(54) CRYSTALLINE FORM OF (S)-1-PHENYLETHYLAMMONIUM (R)-DIPHENYLMETHANESULPHINYL-ACETATE

(75) Inventors: Giuseppe Barreca, Montevecchia (IT); Pietro Allegrini, San Donato Milanese (IT); Gabriele Razzetti, Sesto San Giovanni (IT)

(73) Assignee: Dipharma Francis S.R.L., Baranzate (IT)

( * ) Notice: Subject to any disclaimer, the term of this patent is extended or adjusted under 35 U.S.C. 154(b) by 557 days.

(21) Appl. No.: 12/264,502

(22) Filed: Nov. 4, 2008

(65) Prior Publication Data

US 2009/0156855 A1 Jun. 18, 2009

(51) Int. Cl.
*C07C 323/00* (2006.01)
*C07C 231/00* (2006.01)

(52) U.S. Cl. ........................................ 562/426; 564/145

(58) Field of Classification Search .................. None
See application file for complete search history.

(56) References Cited

U.S. PATENT DOCUMENTS
4,927,855 A    5/1990  Lafon

FOREIGN PATENT DOCUMENTS
EP    1 503 983        2/2005
WO    03/095423 A1    11/2003

OTHER PUBLICATIONS

Prisinzano et al, Tetrahedron: Asymmetry, Synthesis and Determination of the Absolute Configuration of the Enantiomers of Modafinil, 2004, 15, pp. 1053-1058.*

* cited by examiner

*Primary Examiner* — Paul A Zucker
(74) *Attorney, Agent, or Firm* — Griffin & Szipl, P.C.

(57) ABSTRACT

Novel crystalline hydrate form of (S)-1-phenylethylammonium (R)-diphenyl-methanesulphinyl-acetate and its use in a process for the preparation of (R)-benzhydrylsulphinylacetamide.

13 Claims, 2 Drawing Sheets

Figure 1:
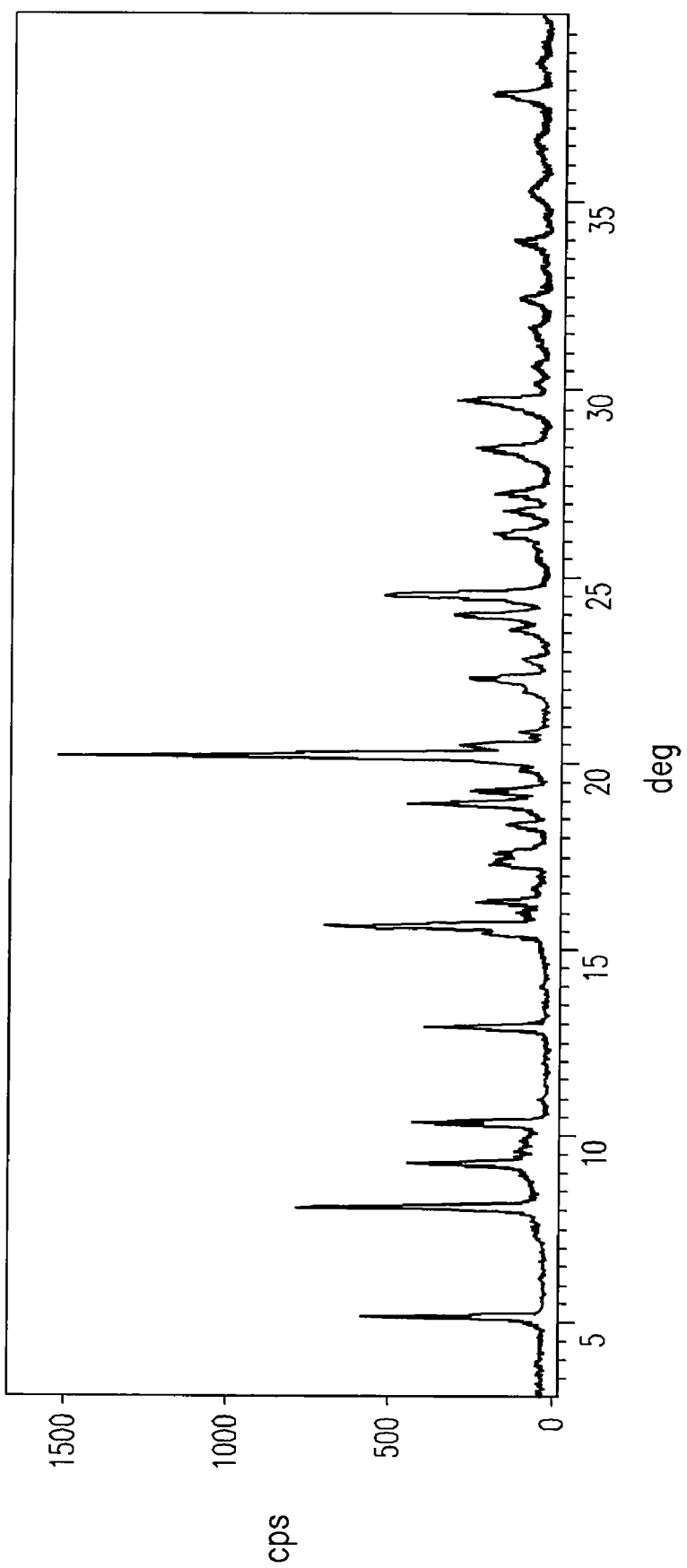

CRYSTALLINE FORM OF (S)-1-PHENYLETHYLAMMONIUM (R)-DIPHENYLMETHANESULPHINYL-ACETATE

This application claims priority from European Patent Application No. 07021472.1, filed Nov. 5, 2007, the entire disclosure of which is incorporated herein by reference.

FIELD OF THE INVENTION

The present invention relates to a novel crystalline hydrate form of (S)-1-phenylethylammonium (R)-diphenyl-methanesulphinyl-acetate and its use in a process for the preparation of (R)-benzhydrylsulphinylacetamide.

TECHNOLOGICAL BACKGROUND (R)-benzhydrylsulphinylacetamide, also defined as (R)-modafinil or Armodafinil, having the following formula (I)

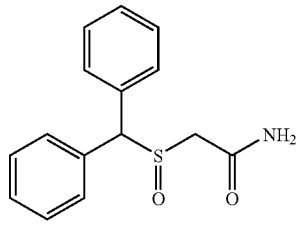

(I)

is a compound endowed with central nervous system stimulating activity. Its preparation as described by U.S. Pat. No. 4,927,855 comprises reacting (±)-benzhydrylsulphinylacetic acid with (−)-α-methylbenzylamine (i.e. (S)-1-phenylethylamine), converting the resulting salt (S)-1-phenylethylammonium (R)-diphenyl-methanesulphinyl-acetate to (R)-benzhydrylsulphinylacetic acid, and subjecting the resulting (R)-benzhydrylsulphinylacetic acid to amidation reaction with gaseous ammonia.

In particular, preparation of (S)-1-phenylethylammonium (R)-diphenyl-methanesulphinyl-acetate, having m.p. 148-150° C., is described in step a) of preparation 1 of the above patent. It will be appreciated that such step suffers, among the others, from the following drawbacks:
- the reaction mixture is very diluted, in fact the ratio between the amount of water and the amount of (±)-diphenyl-methanesulphinyl-acetic acid is about 28.7. Because of its great volume, when carried out in large scale production, the reaction needs large reaction vessels, thus affording a volumetric productivity not higher than 6%; and
- to achieve the required enantiomeric purity degree, the resulting (R)-benzhydrylsulphinylacetic acid needs to be subjected to two recrystallizations, which are very time consuming.

Similarly, Tetrahedron: Asymmetry, 15 (2004) 1053-1058 describes the preparation of anhydrous crystalline (S)-1-phenylethylammonium (R)-diphenyl-methanesulphinyl-acetate.

The inventors of the present invention have surprisingly found that such drawbacks can be overcome by making use of a different reaction medium, thus affording also a novel crystalline hydrate form of (S)-1-phenylethylammonium (R)-diphenyl-methanesulphinyl-acetate, which allows to obtain (R)-modafinil with a greater purity degree.

BRIEF DISCLOSURE OF THE FIGURE AND ANALYTIC METHODS

The crystalline hydrate form of (S)-1-phenylethylammonium (R)-diphenyl-methanesulphinyl-acetate, hereafter Form A, was characterized by X-ray powder diffraction (XRPD) and by differential scanning calorimetry (DSC). The water content in the compound was determined by titration with Karl-Fischer technique.

The X-ray diffraction spectrum (XRPD) was recorded with an APD 2000 θ/θ automatic diffractometer for powders and liquids (Ital-Structures), under the following operative conditions: CuK α radiation ($\lambda$=1.5418 Å), scanning with angular interval 3-40° in 2θ, with angular step of 0.03° for a time of 1 sec.

DSC thermogram was recorded with a Mettler-Toledo differential scansion calorimeter DSC 822, under the following operative conditions: aluminum capsules, 30-400° C. range with increase of 10° C./min, under nitrogen as purging gas (80 ml/min).

FIG. 1: XRPD spectrum of (S)-1-phenylethylammonium (R)-diphenyl-methanesulphinyl-acetate, Form A.

Figure 2:
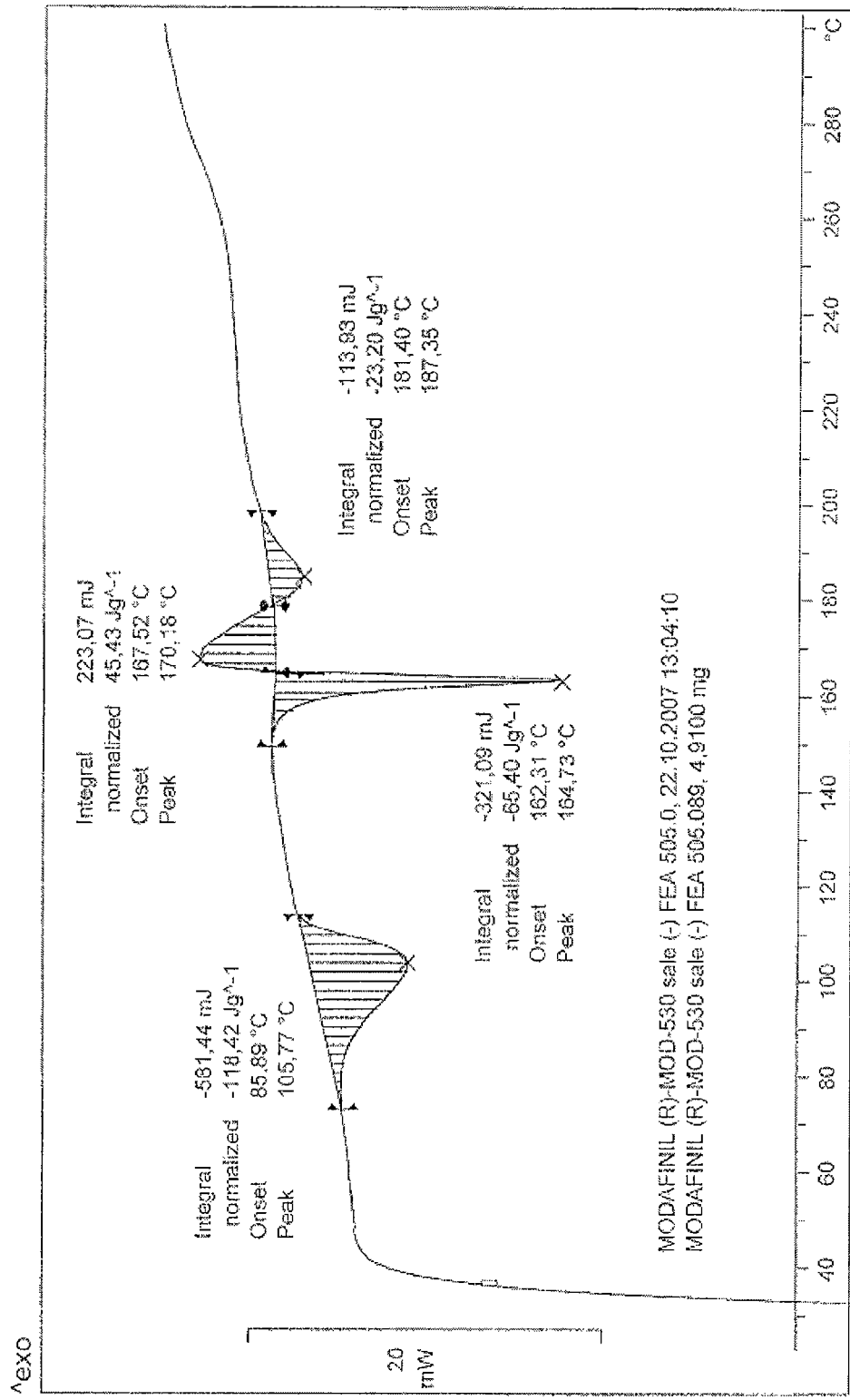

FIG. 2: DSC thermogram of (S)-1-phenylethylammonium (R)-diphenyl-methanesulphinyl-acetate, Form A.

DETAILED DISCLOSURE OF THE INVENTION

A first object of the present invention is (S)-1-phenylethylammonium (R)-diphenyl-methanesulphinyl-acetate, in the crystalline hydrate Form A. Said hydrate form has water content approximately ranging from 3.8 to 5.0%, preferably approximately from 4.1 to 4.7%, so that it can be defined a substantially monohydrate form. Said substantially monohydrate Form A has an XRPD spectrum substantially as shown in FIG. 1, wherein the most intense diffraction peaks fall at 5.2; 8.1; 9.3; 10.4; 12.9; 15.7; 18.9; 20.2; 24.5; 29.7±0.20 in 2θ; and a DSC thermogram substantially as reported in FIG. 2, wherein there are three endothermic peak at about 106; 165 and 187° C. and an exothermic peak at about 170° C. The melting point is 160±1° C.

Compound (S)-1-phenylethylammonium (R)-diphenyl-methanesulphinyl-acetate, in the crystalline hydrate Form A, can be prepared a process comprising:
- dispersing (S)-1-phenylethylamine, (±)-diphenyl-methanesulphinyl-acetic acid and triethylamine in water;
- heating said dispersion to dissolve the reagents;
- cooling the solution to precipitate (S)-1-phenylethylammonium (R)-diphenyl-methanesulphinyl-acetate in crystalline form; and
- recovering the resulting solid.

The ratio between the moles of (S)-1-phenylethylamine and the ones of (±)-diphenyl-methanesulphinyl-acetic acid can range about from 0.4 to 1.00, preferably about from 0.4 to 0.8.

The ratio between the moles of triethylamine and the ones of (±)-diphenyl-methanesulphinyl-acetic acid can range about from 0.05 to 0.6, preferably about from 0.2 to 0.6.

The concentration as w/v of (±)-diphenyl-methanesulphinyl-acetic acid in water can range about from 10% to 30%, preferably about 25%.

The dispersion is stirred and heated to a temperature higher than 20° C., preferably to approximately 65-75° C., to promote dissolution of all the reacting compounds. The resulting solution is left to stand and cooled to a temperature lower than 65° C., preferably from about 20 to 0° C., in particular from about 0 to 5° C., for a time ranging from about 1 to 8 hours, preferably approximately ranging from about 2 to 4 hours, thereby separating (S)-1-phenylethylammonium (R)-diphenyl-methanesulphinyl-acetate salt in the crystalline hydrate Form A. If desired, according to one aspect of the invention, the solution can be cooled a first time to about 60-50° C. to form a precipitate, heated again to about 65-70° C. to obtain a fluid dispersion, and cooled again to about 0-5° C., for a time ranging from about 1 to 8 hours, preferably approximately ranging from about 2 to 4 hours, to form a precipitate of (S)-1-phenylethylammonium (R)-diphenyl-methanesulphinyl-acetate salt in the crystalline hydrate Form A. Alternatively the solution can be seeded with a previously obtained small amount of crystalline Form A to promote crystallization, as known in the art.

The crystalline Form A can be recovered with known techniques, such as filtration or centrifugation, preferably by filtration, followed by drying under vacuum.

The terms "approximately" and "about" as used herein mean±10%.

The process of the invention, affording (S)-1-phenylethylammonium (R)-diphenyl-methanesulphinyl-acetate salt in the crystalline hydrate Form A, allows to purify such intermediate product from any impurity formed during the process for its synthesis, deriving from both parasitic reactions and degradation of the product itself.

Compound (S)-1-phenylethylammonium (R)-diphenyl-methanesulphinyl-acetate, in the crystalline hydrate Form A, can be then converted according to known methods to (R)-benzhydrylsulphinylacetic acid. The acid thus obtained has an enantiomeric purity equal to or higher than 95%, preferably equal to or higher than 98%. It will be appreciated that these results can be achieved without the need of further purifications, contrary to preparation 1 of U.S. Pat. No. 4,927,855 where two recrystallizations are needed.

(R)-benzhydrylsulphinylacetic acid, thus obtained, can be converted to (R)-benzhydrylsulphinylacetamide, i.e, (R)-modafinil, according to known methods, for instance by treatment with a condensing agent and ammonia as described in EP 1 503 983. (R)-modafinil, thus obtained, has an enantiomeric purity degree equal to or higher than 98%, preferably equal to or higher than 99%. That is a purity degree complying with the regulatory requirements for pharmaceutical products.

Accordingly, a further object of the invention is a process for preparing (R)-modafinil having an enantiomeric purity equal to or higher than 99%, comprising reacting (±)-benzhydrylsulphinylacetic acid with (S)-1-phenylethylamine, converting the resulting salt (S)-1-phenylethylammonium (R)-diphenyl-methanesulphinyl-acetate to (R)-benzhydrylsulphinylacetic acid, and subjecting the resulting (R)-benzhydrylsulphinylacetic acid to amidation reaction with ammonia, characterized in that:

compound (S)-1-phenylethylammonium (R)-diphenyl-methanesulphinyl-acetate is obtained in the crystalline hydrate Form A, by a process comprising:
  dispersing (S)-1-phenylethylamine, (±)-diphenyl-methanesulphinyl-acetic acid and triethylamine in water;
  heating said dispersion to dissolve the reagents;
  cooling the solution to precipitate (S)-1-phenylethylammonium (R)-diphenyl-methanesulphinyl-acetate in crystalline form; and
  recovering the resulting solid.

Conversion of salt (S)-1-phenylethylammonium (R)-diphenyl-methanesulphinyl-acetate to (R)-benzhydrylsulphinylacetic acid can be carried out according to known methods, e.g. as disclosed by U.S. Pat. No. 4,927,855. Analogously, amidation reaction of (R)-benzhydrylsulphinylacetic acid with ammonia, can be carried our for instance as disclosed by U.S. Pat. No. 4,927,855 or EP 1 503 983.

(R)-Modafinil obtained according to the process of the invention has a mean particle size $D_{50}$ approximately ranging from 400 to 600 μm., preferably about 500 μm which can be further reduced, for example by a fine grinding process according to known techniques. Said compound usually has a particulate having a D[4,3] mean diameter approximately ranging from 240 to 300 μm, typically around 270 μm. If desired, the mean diameter can be reduced according to known methods, typically by fine grinding, thereby obtaining a product with a mean diameter lower than 40 μm, preferably ranging from 1 to 20 μm.

A further object of the invention is a pharmaceutical composition comprising (R)-modafinil, for example as obtainable according to the process of the present invention, having a mean particle size $D_{50}$ approximately ranging from 400 to 600 μm, and an enantiomeric purity equal to or higher than 99%, and a pharmaceutically acceptable carrier and/or excipient.

The following example illustrates the invention.

EXAMPLE

Preparation of Compound
(S)-1-Phenylethylammonium
(R)-Diphenyl-Methanesulphinyl-Acetate, in the
Crystalline Hydrate Form A (±)-Diphenyl-methanesulphinyl-acetic acid (400 g), (S)-1-phenylethylamine (106 g) and triethylamine (66.3 g) are dispersed in water (1600 ml). The reacting mixture is heated to about 70° C. and kept under stirring at such temperature till complete dissolution. The solution is cooled to about 55° C. thus obtaining an abundant precipitation of the product. The whole is heated again to about 65-68° C. to obtain a fluid mixture, which is cooled again to about 0-5° C. The mixture is kept at such temperature over about 1 hour. After that the precipitate is filtered off and washed three times with water (200 ml). The product is dried under vacuum at 50° C. overnight.

The resulting product (277 g) owns an enantiomeric purity of 98.6%; and a water content, determined according to Karl Fischer, of approximately 4.5%; m.p. 160±1° C. The same title compound has an XRPD spectrum substantially as reported in FIG. 1 and a DSC thermogram substantially as shown in FIG. 2, which prove that the compound is crystalline.

The invention claimed is:

1. (S)-1-phenylethylammonium (R)-diphenyl-methanesulphinyl-acetate, in crystalline hydrate form, having an XRPD spectrum wherein the most intense diffraction peaks fall at 5.2; 8.1; 9.3; 10.4; 12.9; 15.7; 18.9; 20.2; 24.5; 29.7 ± 0.2° in 2 θ.

2. (S)-1-phenylethylammonium (R)-diphenyl-methanesulphinyl-acetate, according to claim 1, wherein the water content approximately ranges from 3.8 to 5.0%.

3. (S)-1-phenylethylammonium (R)-diphenyl-methanesulphinyl-acetate, according to claim 1, having a DSC thermogram spectrum, showing three endothermic peak at about 106; 165 and 187° C. and an exothermic peaks at about 170° C.

4. (S)-1-phenylethylammonium (R)-diphenyl-methanesulphinyl-acetate, according to claim 3, having m.p. 160±1° C.

5. A process for the preparation of (S)-1-phenylethylammonium (R)-diphenyl-methanesulphinyl-acetate in the crystalline hydrate form, as defined in claim 1, wherein the process comprises the steps of:
(a) dispersing (S)-1-phenylethylamine, (±)-diphenyl-methanesulphinyl-acetic acid and triethylamine in water;
(b) heating said dispersion to dissolve the reagents;
(c) cooling the solution to precipitate (S)-1-phenylethylammonium (R)-diphenyl-methanesulphinyl-acetate in crystalline form; and
(d) recovering the resulting solid.

6. A process according to claim 5, wherein the ratio between the moles of (S)-1-phenylethylamine and the ones of (±)-diphenyl-methanesulphinyl-acetic acid range about from 0.4 to 1.00.

7. A process according to claim 5, wherein the ratio between the moles of triethylamine and the ones of (±)-diphenyl-methanesulphinyl-acetic acid ranges about from 0.05 to 0.6.

8. A process according to claim 5, wherein the concentration as w/v of (±)-diphenyl-methanesulphinyl-acetic acid in water can range about from 10% to 30%.

9. (S)-1-phenylethylammonium (R)-diphenyl-methanesulphinyl-acetate, according to claim 2, having a DSC thermogram spectrum, showing three endothermic peaks at about 106; 165 and 187° C. and an exothermic peaks at about 170° C.

10. A process according to claim 8, wherein the concentration as w/v of (±)-diphenyl-methanesulphinyl-acetic acid in water is about 25%.

11. A process for preparing (R)-modafinil having an enantiomeric purity equal to or higher than 99%, wherein the process comprises the steps of:
(a) reacting (±)-benzhydrylsulphinylacetic acid with (S)-1-phenylethylamine;
(b) converting the resulting salt (S)-1-phenylethylammonium (R)-diphenyl-methanesulphinyl-acetate to (R)-benzhydrylsulphinylacetic acid; and
(c) subjecting the resulting (R)-benzhydrylsulphinylacetic acid to amidation reaction with ammonia, wherein compound (S)-1-phenylethylammonium (R)-diphenyl-methanesulphinyl-acetate, in crystalline hydrate form having an XRPD spectrum wherein the most intense diffraction peaks fall at 5.2; 8.1; 9.3; 10.4; 12.9; 15.7; 18.9; 20.2; 24.5; 29.7 ±0.2° in 2θ, is used as an intermediate material.

12. A method for preparing (R)-modafinil having an enantiomeric purity equal to or higher than 99%, wherein the method comprises the steps of:
(a) providing as an intermediate material (S)-1-phenylethylammonium (R)-diphenyl-methanesulphinyl-acetate, in crystalline hydrate form having an XRPD spectrum wherein the most intense diffraction peaks fall at 5.2; 8.1; 9.3; 10.4; 12.9; 15.7; 18.9; 20.2; 24.5; 29.7 ± 0.2° in 2θ; and
(b) converting the intermediate material of step (a) into (R)-modafinil.

13. A process for preparing (R)-modafinil having an enantiomeric purity equal to or higher than 99%, wherein the process for preparing (R)-modafinil comprises the steps of:
(a) reacting (±)-benzhydrylsulphinylacetic acid with (S)-1-phenylethylamine;
(b) converting the resulting salt (S)-1-phenylethylammonium (R)-diphenyl-methanesulphinyl-acetate to (R)-benzhydrylsulphinylacetic acid; and
(c) subjecting the resulting (R)- benzhydrylsulphinylacetic acid to amidation reaction with ammonia, wherein compound (S)-1-phenylethylammonium (R)-diphenyl-methanesulphinyl-acetate is obtained in crystalline hydrate form having an XRPD spectrum wherein the most intense diffraction peaks fall at 5.2; 8.1; 9.3; 10.4; 12.9; 15.7; 18.9; 20.2; 24.5; 29.7 ±0.2° in 2θ, by a second process comprising the steps of
i. dispersing (S)-1-phenylethylamine, (±)-diphenyl-methanesulphinyl-acetic acid and triethylamine in water;
ii. heating said dispersion to dissolve the reagents;
iii. cooling the solution to precipitate (S)-1-phenylethylammonium (R)-diphenyl-methanesulphinyl-acetate in crystalline form; and
iv. recovering the resulting solid.

* * * * *

UNITED STATES PATENT AND TRADEMARK OFFICE
CERTIFICATE OF CORRECTION

| | | |
|---|---|---|
| PATENT NO. | : 8,193,386 B2 | Page 1 of 1 |
| APPLICATION NO. | : 12/264502 | |
| DATED | : June 5, 2012 | |
| INVENTOR(S) | : Barecca et al. | |

It is certified that error appears in the above-identified patent and that said Letters Patent is hereby corrected as shown below:

Title Page should read

(30)   Foreign Application Priority Data

November 5, 2007   (EP)   ................................................07021472.1

Signed and Sealed this
Eleventh Day of September, 2012

David J. Kappos
*Director of the United States Patent and Trademark Office*